United States Patent [19]
Katzschmann

[11] B 3,944,602
[45] Mar. 16, 1976

[54] PROCESS FOR THE PREPARATION OF TEREPHTHALIC ACID

[75] Inventor: Ewald Katzschmann, Witten-Bommern, Germany

[73] Assignee: Chemische Werke Witten GmbH, Germany

[22] Filed: Sept. 7, 1971

[21] Appl. No.: 178,475

[44] Published under the Trial Voluntary Protest Program on January 28, 1975 as document no. B 178,475.

Related U.S. Application Data
[63] Continuation of Ser. No. 568,405, July 28, 1966, abandoned.

[30] Foreign Application Priority Data
July 28, 1965 Germany............................ 1259326

[52] U.S. Cl. ............................................... 260/525
[51] Int. Cl.$^2$..................... C07C 63/26; C07C 51/42
[58] Field of Search .................................... 260/525

[56] References Cited
UNITED STATES PATENTS

| | | | |
|---|---|---|---|
| 2,572,710 | 10/1951 | Emerson.............................. | 260/525 |
| 2,894,978 | 7/1959 | Katzschmann...................... | 260/525 |
| 3,171,856 | 3/1965 | Kurtz................................... | 260/525 |
| 3,364,256 | 1/1968 | Ichikawa et al..................... | 260/525 |

*Primary Examiner*—Lorraine A. Weinberger
*Assistant Examiner*—Richard D. Kelly
*Attorney, Agent, or Firm*—Craig & Antonelli

[57] ABSTRACT

An after-treatment or purification process for oxidation products produced by the air oxidation of a mixture of p-toluic acid methyl ester and p-xylene to provide terephthalic acid wherein the oxidation products are heated to an elevated temperature under pressure and a substance such as p-xylene, water, a lower carboxylic acid containing from 1 – 4 carbon atoms and mixtures thereof is added thereto. Subsequently, the desired terephthalic acid is separated from the resultant reaction mixture.

16 Claims, No Drawings

PROCESS FOR THE PREPARATION OF TEREPHTHALIC ACID

This is a continuation of application Ser. No. 568,405 filed July 28, 1966 now abandoned.

This invention relates to an improved process for the preparation of terephthalic acid. More particularly, it relates to a process for the production of terephthalic acid by an after-treatment of certain oxidation products. Even more particularly, the invention relates to a process for the preparation of terephthalic acid which involves an after-treatment of the oxidation products obtained in accordance with the process described in German Pat. No. 1,041,945 (which corresponds to U.S. Pat. No. 2,894,978).

The oxidation of p-xylene with oxidizing agents containing at least one bound oxygen, such as nitric acid, for example, gives an end product terephthalic acid which must be subjected to an intensive purification in case such terephthalic acid is to be used in the preparation of, for example, alkyd resins or polyester fibers, filaments or films.

The oxidation of p-xylene in the liquid phase with oxygen or air at elevated temperatures in the presence of soluble catalysts gives, as a practical matter, only p-toluic acid as the end product. Correspondingly, the oxidation of p-xylene in acetic acid and in the presence of soluble catalysts and so-called initiators, such as bromine compounds, for example, yields predominantly terephthalic acid in addition to p-toluic acid. However, strict requirements in properties must be satisfied by the material of the vessel or container employed when using, for example, acetic acid and bromine compounds. Thus, temperatures around 200°C. and pressures around 20 to 30 atmospheres are necessary in order to obtain the terephthalic acid stage. And, in order to attain a technically utilizable terephthalic acid, additional purification steps are required.

In an attempt to overcome some of these and other problems, German Pat. No. 949,564, proposes the further oxidation of p-toluic acid up to the terephthalic acid stage by oxidation of the p-toluic acid methyl ester. While it is very difficult to further oxidize free p-toluic acid, the oxidation of the p-toluic acid methyl ester to the terephthalic acid monomethyl ester proceeds with great ease.

The joint oxidation of p-xylene together with p-toluic acid methyl ester in accordance with German Pat. No. 1,041,945, simultaneously yields unreacted p-toluic acid methyl ester, p-toluic acid, terephthalic acid monomethyl ester and free terephthalic acid. During the proposed subsequent esterification, a mixture of p-toluic acid methyl ester and terephthalic acid dimethyl ester is obtained which is separated by distillation. The p-toluic acid methyl ester is returned to the oxidation step, and the terephthalic acid dimethyl ester is isolated for further treatment to yield the corresponding polyester. The end product of this described process is characterized by a high degree of purity since no difficulty removable chemicals producing secondary reactions are employed in the course thereof. The free terephthalic acid obtained in the process according to said German Pat. No. 1,041,945, is not isolated as such. Instead, it is esterified with methanol during the course of the process.

For specific purposes, for example, in the preparation of alkyd resins, the industry starts with free terephthalic acid for technical and economic reasons. The purity of the terephthalic acid which may be achieved with the means and processes known to date suffices for such purposes. In a few instances, so-called "fiber-pure" or grade terephthalic acid has been prepared which, by direct reaction with ethylene glycol, may be processed to give polyesters which are suitable for making fibers. However, attempts to isolate the terephthalic acid produced in accordance with the process of German Pat. No. 1,041,945, from the oxidation products in which it is present in an amount of from 16 to 20 percent by weight and to utilize the same for technical purposes or applications has failed because of the unsatisfactory quality thereof. The free terephthalic acid which is separated as a methanol-insoluble matter or a xylene insoluble matter has a saponification of from 630 to 645; the calculated saponification number thereof is 676. Simple purification methods, such as reprecipitation above the ammonium or alkali metal salt, acid washings and the like, fail to a lesser or greater extent in achieving the quality of terephthalic acid needed. Thus, the task of isolating a terephthalic acid which is largely technically pure or is adapted to be readily further purified from the oxidation products obtained in accordance with the process of German Pat. No. 1,041,945, has remained without solution, even though there is a technical and economic need therefor in view of the advantages of this process as discussed above.

One of the objects of the present invention is to provide an improved process for the preparation of terephthalic acid which overcomes the disadvantages and deficiencies of the prior art methods.

Another object of the present invention is to provide a process for producing terephthalic acid of high purity whch may be carried out in an efficacious and simple manner.

A further object of the invention is to provide terephthalic acid of high purity which may be used in a variety of applications.

These and other objects and advantages of the present invention will become apparent to those skilled in the art from a consideration of the following specification and claims.

In accordance with the present invention, it has been found that terephthalic acid of high quality may be isolated from the oxidation products obtained according to the process described in the said German Pat. No. 1.041,945, if these oxidation products are subjected to the subsequent or after-treatment described herein. This subsequent treatment comprises mixing the obtained oxidation product with p-xylene, water, or a lower carboxylic acid (80–100 percent) having from 1 to 4 carbon atoms, or mixtures thereof, and simultaneously raising the temperature of the resultant solution to from 210°–280°C., preferably 220°–250°C.

Mixing of the oxidation product with the said additives may be effected either after an intermediate storage or directly upon the completion of the oxidation, either in the oxidation vessel itself or in one or a plurality of suitable vessels. Such "vessels" may also be a system of pipes. The amount of additive to be employed may range, for example, up to about 50 percent by weight of p-xylene, up to about 15 percent by weight of water and up to about 30 percent by weight of a lower carboxylic acid, such as acetic acid, the percentages being based upon the weight of the oxidation product.

In carrying out the steps of the present invention, it is expedient to maintain the pressure which was employed during the oxidation. The temperature employed as well as the period of time of after-treatment are important in achieving the beneficial results of the improvement of the present invention. Moreover, the particular admixture employed has an effect upon the purity of the resultant terephthalic acid as well as upon the amount thereof. For example, an addition of from 2 to 10 percent by weight of water, based on the weight of oxidation product, produces an increase of isolable terephthalic acid of from 40 to 60 percent by weight. Other advantages of the after-treatment of the present invention reside in the improved manipulation and better feed of the oxidation products as well as upon the color of the terephthalic acid obtained. Thus, for example, the saponification number of the terephthalic acid obtained in accordance with the method of working proposed by the present invention is 676. As mentioned above, the calculated saponification number is also 676.

The amount of time of subsequent treatment, once the appropriate temperature has been attained, should be between ½ hour and 4 to 5 hours. On the average, 1 hour is sufficient. If the reaction is controlled appropriately, the heating uptime thereof may suffice to achieve the effect according to the present invention.

The separation of the terephthalic acid from the subsequently treated oxidation product is carried out following the subsequent treatment either directly from the hot oxidation product or from the hot suspension which is produced by the addition of an organic solvent thereto. If the latter method is used, an organic solvent is employed in which all of the components, with the exception of terephthalic acid, such as p-toluic acid, p-toluic acid methyl ester, terephthalic acid monomethyl ester and by-products, are soluble. A suitable solvent for this purpose is p-xylene.

While the isolation of the free terephthalic acid from an untreated oxidation product, i.e., not subsequently treated as described in the present application, requires approximately from 8 to 10 times the amount thereof by weight of p-xylene in order to obtain a separation of the terephthalic acid from the by-products, only from 2 to 3 times the amount of terephthalic acid by weight of p-xylene is sufficient for the separation of the free terephthalic acid formed in accordance with the after-treatment process of the present invention. The easier separability is noticeably apparent since the suspension prepared from a subsequently treated oxidation product, in accordance with the present invention, displays a "sandy" character in p-xylene. On the other hand, a suspension obtained from an oxidation product which has not been subjected to the aftertreatment described herein, and although containing more solvent, has a "greasy" or "smeary" character.

The separation of the terephthalic acid from the oxidation product, the solution or the suspension is effected by decanting, filtering or centrifuging the same while hot. Quite suitable therefor is a so-called "Seitz filter". Depending upon the particular work-up method and conditions employed, scaling centrifuges equipped with a washing device may also be advantageously employed.

Terephthalic acid obtained from oxidation products in accordance with the process of German Pat. No. 1,041,945, which has not been subsequently treated in accordance with the present invention shows a distinctly violet-gray discoloration and has a saponification number of approximately 635. However, terephthalic acid obtained from substantially treated oxidation products shows only a very faint coloration and a saponification number of from 675–676 (calculated: 676).

The resultant filtrate is employed either directly in further oxidations or is brought, by distillation of the p-xylene, to the quantitative proportion required in accordance with German Pat. No. 1,041,945. The filtrate may also be esterified with methanol, either in the presence of the p-xylene, a portion of the p-xylene, or after the complete distillation of the p-xylene. Such an esterification may be carried out either after each batch or at intervals in order to convert the p-toluic acid present into the oxidizable p-toluic acid methyl ester. This represents a summary of the operational steps which may be employed, however, it is to be understood that correspondingly modified working steps may be utilized for particular operational or economic reasons.

The terephthalic acid obtained in accordance with the subsequent treatment proposed by the present invention may be employed, as mentioned above, without any further purification for many purposes, such as, for example, in the preparation of alkyd resins, which is a well known procedure. If it is desired to prepare polyester fibers by the direct reaction of the terephthalic acid with ethylene glycol, it may be necessary to additionally purify the same according to one of the processes known in the prior art therefor.

Table 1 shows some specific embodiments of the present invention, as well as some comparative experiments with respect thereto. These Examples are given merely as illustrative of the present invention and are not to be considered as limiting. Unless otherwise noted, the percentages therein are by weight, based on the weight of oxidation product employed.

TABLE 1

| Experiment No. | Subsequent Treatment | | Time (hours) | Temperature (°C.) | Pressure (atmospheres) | Terephthalic Acid Obtained | | Oxidation Product Designation |
|---|---|---|---|---|---|---|---|---|
| | Additions (%) | | | | | Yield (%) | Saponification No. | |
| 1 | — | | — | — | — | 20.3 | 641 | 5/117 |
| 2 | — | | — | — | — | 16.5 | 640 | 6/104 |
| 3 | — | | — | — | — | 16.0 | 633 | 7/8 |
| 4 | 15% | p-xylene | 4 | 250 | 7 | 24.2 | 676 | 5/117 |
| 5 | 20% | p-xylene | 1 | 275 | 10.5 | 21.2 | 676 | 6/104 |
| 6 | 100% | glacial acetic acid | 1 | 250 | 16.0 | 16.8 | 663 | 6/104 |
| 7 | 33% | do. | 1 | 250 | 16.0 | 19.3 | 673 | 6/104 |
| 8 | 10% | do. | 2 | 250 | 6.0 | 22.6 | 676 | 6/104 |
| 9 | 10% | do. | ½ | 275 | 10.5 | 22.2 | 676 | 6/104 |
| 10 | 5% | water | 1 | 200 | 7.0 | 24.3 | 649 | 5/117 |
| 11 | 5% | water | 2 | 200 | 7.0 | 29.0 | 659 | 5/117 |

TABLE 1-continued

| Experiment No. | Additions (%) | | Time (hours) | Temperature (°C.) | Pressure (atmospheres) | Terephthalic Acid Obtained Yield (%) | Saponification No. | Oxidation Product Designation |
|---|---|---|---|---|---|---|---|---|
| 12 | 5% | water | 3 | 200 | 7.0 | 30.5 | 662 | 5/117 |
| 13 | 5% | water | 2 | 210 | 8.5 | 30.3 | 676 | 5/117 |
| 14 | 5% | water | 1 | 225 | 9.0 | 28.5 | 672 | 5/117 |
| 15 | 5% | water | 2 | 225 | 9.0 | 30.5 | 676 | 5/117 |
| 16 | 5% | water | ½ | 240 | 11.5 | 28.0 | 676 | 7/8 |
| 17 | 5% | water | ½ | 250 | 12.0 | 25.2 | 676 | 5/117 |
| 18 | 5% | water | 2 | 250 | 12.0 | 32.6 | 676 | 5/117 |
| 19 | 5% | water | 4 | 250 | 12.0 | 31.6 | 676 | 5/117 |
| 20 | 7.5% | water | 4 | 250 | 13.0 | 32.6 | 676 | 7/8 |
| 21 | 10% | water | 2 | 250 | 13.0 | 29.2 | 676 | 6/104 |
| 22 | 15% | water | 4 | 250 | 13.0 | 32.9 | 676 | 5/117 |
| 23 | 30% 3% | p-xylene water | 2 | 250 | 18.0 | 21.4 | 676 | 6/104 |
| 24 | 16% 5% | glacial acetic acid water | 1 | 250 | 16.0 | 30.4 | 676 | 6/104 |
| 25 | 5% | water | ½ | 275 | 20.0 | 27.4 | 676 | 6/104 |

As noted above, the present invention relates to an improvement of the process described in the present applicant's German Pat. No. 1,041,945, issued Oct. 30, 1958. The details of this process may be obtained specifically from this patent, but certain features thereof are described hereinbelow in order to facilitate a better understanding of the present invention.

The said patented process involves conducting the combined oxidation of xylene or the isomeric mixtures thereof and the esters of the corresponding toluic acids produced therefrom in such a manner that the ester is present in excess at the beginning thereof, the oxidation being controlled suitably in such a way that substantially as much toluic acid is formed by the oxidation of the xylenes as esters of the toluic acids are oxidized to phthalic acid monoesters. Thereafter, the oxidation reaction mixture is esterified, the diester of the benzene dicarboxylic acid is separated, and the obtained toluic acid ester is oxidized, together with fresh xylene, in the above-described manner. It is particularly advantageous to control the oxidation in such a manner that when the desired degree of oxidation is reached, there is practically no xylene left in the reaction mixture.

The advantage of the combined oxidation of xylenes and toluic acid esters resides, on the one hand, in that when the oxidation is terminated, there is present essentially a mixture of the oxidation products (toluic acid and benzene dicarboxylic acid monoester) together with unreacted toluic acid ester, which is endowed with a considerably higher dissolving power for the oxidation products than the xylenes, so that it is possible to continue the oxidation process to higher oxidation degrees or to obtain, at the same degree of oxidation, substantially more readily fluid and thus more easily manipulatable reaction mixtures than in the case where the xylenes are present as the solvent remaining upon the termination of the oxidation. On the other hand, by means of this process, an extraordinarily simple operation is attained, since the reaction vessel, as well as the esterification system, process continually the same amounts of substances of the same type. A further advantage of oxidizing xylenes in an excess of toluic acid esters resides in that less by-products are formed which are produced in the oxidation of the xylenes.

This process is conducted under the reaction conditions conventional for the oxidation of alkylaromatic hydrocarbons and esters of alkylaromatic carboxylic acids, at a temperature between 80° and 250°C., preferably between 110° and 200°C., at normal or elevated pressure and in the presence of catalysts. Preferred catalysts are metal compounds which are soluble in the reaction mixture, such as the various valence states of cobalt or manganese, for example, salts of cobalt with fatty acids of from 6 to 12 carbon atoms or of aromatic carboxylic acids, such as toluic acid. The process may be carried out batch-wise as well as continuously.

The concentration of the xylenes used in the toluic acid esters is actually of no decisive importance in this process. However, since one of the advantages of the process lies in the high dissolving power of the ester for the oxidation products, it is preferable to select a concentration thereof which is relatively high. Thus, for example, in the case of oxidizing p-xylene in a mixture with methyl-p-toluate, this concentration preferably ranges from about 35–40 parts of xylene 65–60 parts of ester, because the amount of ester serving as the dissolving or dispersing agent passing through the esterification stage unchanged is then small.

Another point to be noted with respect to this process is that the condition that there be formed as much toluic acid by oxidizing the corresponding xylene as esters of the toluic acids are oxidized to phthalic acid monoesters needs to be maintained only within certain limits. If, for example, in one of the batches, less toluic acid ester has been oxidized than xylene, a larger quantity of ester is present after the esterification step, and this quantity can be oxidized, in the next batch, with correspondingly less xylene, so that a certain self-regulation is obtained.

It should also be noted that this process can be carried out with the isomeric xylenes per se or with mixtures thereof, as well as the various isomeric toluic acid esters which can likewise be used each per se or in a mixture with one another.

The following Examples serve to illustrate the process in accordance with German Pat. No. 1,041,945, of which the present invention is an improvement.

EXAMPLE I

At the beginning, a mixture of 1.2 kg. p-xylene (96 percent solution) and 4.8 kg. of pure methyl-p-toluate was charged into a compression-proof oxidation vessel of a capacity of 10 liters, this vessel being connected with a reflux condenser with a water trap. This mixture was mixed with 12 g. of the cobalt salt of preliminary run coconut oil fatty acid as the catalyst. The oxidation was conducted at 5 atmospheres excess pressure with 1.08 m³/hr of air (measured at normal pressure) at 160°C., until after 20 hours the acid number of the reaction mixture had risen to 205. At this instant, there was practically no xylene left in the reaction mixture. The reaction product was esterified by treating the same for 30 hours with 20l. of methanol at 65°C. in the presence of 180 g. of sulfuric acid (98 percent). After cooling, 2.1 kg. of dimethyl terephthalate (saponification value = 578; acid number = 0.6; m.p. = 140.5°C.) was filtered off; the filtrate was freed from excess methanol, and the residue was freed from sulfuric acid by washing. There was obtained 4.88 kg. of methyl toluate (saponification value = 402; acid number=6). The methyl toluate was mixed with 1.12 kg. of fresh xylene, as well as 5 g. of catalyst, and the oxidation was continued as described above. After 18 hours, the oxidation mixture had reached the acid number of 288 and the saponification value of 495. The esterification process as described above was conducted, and there was obtained 2.75 kg. of dimethyl terephthalate. The remaining p-toluic acid methyl ester was increased to a volume of 6 kg. by adding p-xylene thereto, and the oxidation was continued.

EXAMPLE II

Into a compression-proof oxidation vessel having a capacity of 60 liters and otherwise constructed as set forth in Example I, a mixture of 10 kg. of p-xylene (96 percent) and 20 kg. of industrial methyl-p-toluate was charged and mixed with 60 g. of the cobalt salt of preliminary run coconut oil fatty acid as the catalyst. The oxidation was conducted at 1.5 atmospheres excess pressure with 5.4 m³/hr of air at 140°C. until, after 18 hours, the acid number of the reaction mixture had reached 305. At this point, no xylene was present in the reaction mixture. The reaction mixture was esterified with methanol under pressure, and the esterification product was subsequently introduced into methanol for separating the terephthalic acid dimethyl ester. There was filtered off 14.3 kg. of dimethyl terephthalate (acid number = 1.2; saponification value = 576; m.p. = 140°C.). The remaining toluic acid methyl ester was charged again with p-xylene to 30 kg. and further oxidized, as described above.

EXAMPLE III

Into a compression-proof oxidation vessel having a capacity of 60 liters, 15 kg. of m-xylene (98 percent) and 30 kg. of industrial m-toluic acid methyl ester were charged. The oxidation vessel was provided with a feed conduit for air, a heating device, a cooling device, and a reflux condenser with a water trap. The waste air was passed through a tower charged with active charcoal. The catalyst used was 67.5 g. of the cobalt salt of preliminary run coconut oil fatty acid. Additionally, 2.5 kg. of m-xylene was filled into the water trap. At a pressure of 1.5 atmospheres gauge and a temperature of 140°C., 3 liters per minute per kg. of air was passed through the reaction mixture. After 12 hours, the oxidation was terminated. There was obtained 49.02 kg. of oxidation mixture (acid number = 305; saponification value = 510). The mixture did not contain any residual m-xylene. From the activated charcoal, 2.43 kg. of xylene could be recovered. Some of the mixture adhered to the walls of the reaction vessel. The mixture was esterified under pressure with methanol. The thus-obtained crude ester was of the following composition, in accordance with the analysis thereof:

38.3 percent m-toluic acid methyl ester
53.3 percent isophthalic acid dimethyl ester
7.0 percent higher boiling components.

By distillation, 20.6 kg. of pure isophthalic acid dimethyl ester was obtained (acid number = 0.7; saponification value = 575; m.p. 64°C.).

The distillation forerunnings gave m-toluic acid methyl ester, the distillation intermediate runnings gave m-toluic acid methyl ester and the last distillation runnings were again brought to a volume of 45 kg. by adding m-xylene thereto, and then oxidized as described above. The crude ester resulting therefrom had the following composition:

38.3 percent m-toluic acid methyl ester
53.0 percent isophthalic acid dimethyl ester
7.0 percent higher boiling components By distillation, 22.4 kg. of pure isophthalic acid dimethyl ester was obtained having the same characteristics as above. The process was continued with identical results.

The invention being thus described, it will be obvious that the same may be varied in many ways. Such variations are not to be regarded as a departure from the spirit and scope of the invention, and all such modifications are intended to be included within the scope of the following claims.

I claim:

1. An after-treatment process for oxidation products, that are obtained by the air oxidation of a mixture of p-toluic acid methyl ester in excess and p-xylene and that contain p-toluic acid methyl ester, p-toluic acid, terephthalic acid monomethyl ester and terephthalic acid, to isolate pure terphthalic acid which comprises heating said oxidation products to an elevated temperature and under pressure and adding a substance selected from the group consisting of water, a mixture of p-xylene and water, and a mixture of acetic acid and water and separating the pure terephthalic acid from the reaction mixture.

2. The process of claim 1, wherein said elevated temperature is between about 210° and 280°C.

3. The process of claim 1, wherein said elevated temperature is between about 220° and 250°C.

4. The process of claim 1, wherein the period of time of said after-treatment process ranges from between the necessary heating up time and 5 hours.

5. The process of claim 1, wherein said after-treatment process is carried out continuously.

6. The process of claim 5, wherein said continuous after-treatment process is carried out in a system of pipes.

7. The process of claim 1, wherein said p-xylene is employed in an amount of up to about 50 percent by weight, said water in an amount of up to about 15 percent by weight, and said acetic acid in an amount of up to about 30 percent by weight, said percentages being based upn the weight of the oxidation product.

8. The process of claim 1, wherein said oxidation products contain on the order of from 16 to 20 percent by weight of terephthalic acid.

9. The process of claim 1, wherein said pure terephthalic acid has a saponification number of 676.

10. The process of claim 1, wherein said substance is water.

11. The process of claim 1, wherein said substance is a mixture of p-xylene and water.

12. The process of claim 1, wherein said substance is a mixture of acetic acid and water.

13. An after-treatment process for oxidation products, that are obtained by the air oxidation of a mixture of p-toluic acid methyl ester in excess and p-xylene and that contain p-toluic acid methyl ester, p-toluic acid, terephthalic acid monomethyl ester and terephthalic acid, to isolate pure terephthalic acid which comprises heating said oxidation products to an elevated temperature of between about 210° and 280°C. and under pressure and adding a substance selected from the group consisting of water, a mixture of p-xylene and water, and a mixture of acetic acid and water, the period of time of said after-treatment process ranging from between the necessary heating up time and five hours, and separating the pure terephthalic acid from the reaction mixture.

14. The process of claim 13, wherein said temperature is between about 220° and 250°C.

15. The process of claim 14, wherein said after-treatment process is carried out continuously.

16. The process of claim 13, wherein said p-xylene is employed in an amount of up to about 50 percent by weight, said water in an amount of up to about 15 percent by weight and said acetic acid in an amount of up to about 30 percent by weight, said percentages being based upon the weight of oxidation product.

* * * * *